United States Patent
Jimenez et al.

(10) Patent No.: US 10,213,254 B2
(45) Date of Patent: *Feb. 26, 2019

(54) CATHETER WITH LIQUID-COOLED CONTROL HANDLE

(71) Applicant: BIOSENSE WEBSTER, INC., Diamond Bar, CA (US)

(72) Inventors: Eduardo Jimenez, Fullerton, CA (US); Jeffrey W. Schultz, Chino, CA (US); Rogelio Plascencia, Jr., Rancho Cucamonga, CA (US); Mario Solis, Rancho Cucamonga, CA (US); Arnold Tuason, Claremont, CA (US); Christopher Beeckler, Brea, CA (US); Ariel Garcia, Glendora, CA (US); Assaf Govari, Haifa (IL); Yaron Ephrath, Kakur (IL); Dean Ponzi, Glendora, CA (US)

(73) Assignee: Biosense Webster, Inc., Irvine, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 15/073,510

(22) Filed: Mar. 17, 2016

(65) Prior Publication Data

US 2016/0199129 A1    Jul. 14, 2016

Related U.S. Application Data

(63) Continuation of application No. 14/666,247, filed on Mar. 23, 2015, now Pat. No. 9,289,259, which is a
(Continued)

(51) Int. Cl.
*A61B 18/14* (2006.01)
*A61B 18/12* (2006.01)
*A61B 18/00* (2006.01)

(52) U.S. Cl.
CPC .......... *A61B 18/1492* (2013.01); *A61B 18/12* (2013.01); *A61B 2018/00011* (2013.01);
(Continued)

(58) Field of Classification Search
CPC ............... A61B 18/12; A61B 18/1492; A61B 2018/00011; A61B 2018/00023;
(Continued)

(56) References Cited

U.S. PATENT DOCUMENTS

| | | |
|---|---|---|
| RE34,502 E | 1/1994 | Webster, Jr. |
| 5,360,993 A | 11/1994 | Mine |

(Continued)

FOREIGN PATENT DOCUMENTS

| | | |
|---|---|---|
| JP | 07-027495 A | 1/1995 |
| JP | 2003-505139 A | 2/2003 |

(Continued)

OTHER PUBLICATIONS

English Translation of Examiner's Decision of Refusal issued in Japanese Patent Application No. 2011-244181, dated Mar. 15, 2016, 3 pages.

(Continued)

*Primary Examiner* — Michael Peffley
*Assistant Examiner* — Amanda Zink
(74) *Attorney, Agent, or Firm* — Lewis Roca Rothgerber Christie LLP

(57) ABSTRACT

An electrophysiologic catheter with an improved control handle is provided. The catheter includes a heat transfer assembly to better dissipate heat in the control handle. The heat transfer assembly includes a pump, a reservoir containing a coolant, a heat transfer member, and a coolant transport network transporting coolant between at least the reservoir and the heat transfer member. In one embodiment, the heat transfer member is located within the control handle as a
(Continued)

heat exchanger on the circuit board to receive the coolant for transferring heat from the integrated circuits to the coolant. In another embodiment, the heat transfer member is located on the circuit board directly surrounding the integrated circuits to internally cool the integrated circuit within the control handle. A second heat transfer member is located outside of the control handle as a heat exchanger.

19 Claims, 12 Drawing Sheets

Related U.S. Application Data continuation of application No. 12/942,880, filed on Nov. 9, 2010, now Pat. No. 8,986,303.

(52) U.S. Cl.
CPC ........ *A61B 2018/00023* (2013.01); *A61B 2018/0091* (2013.01); *A61B 2018/00351* (2013.01); *A61B 2018/00577* (2013.01)

(58) Field of Classification Search
CPC ......... A61B 2018/00351; A61B 2018/00577; A61B 2018/0091
See application file for complete search history.

(56) References Cited

U.S. PATENT DOCUMENTS

| | | | |
|---|---|---|---|
| 5,628,771 A * | 5/1997 | Mizukawa | A61B 18/18 606/31 |
| 5,735,846 A | 4/1998 | Panescu et al. | |
| 5,893,885 A | 4/1999 | Webster, Jr. | |
| 5,897,529 A | 4/1999 | Ponzi | |
| 5,964,757 A | 10/1999 | Ponzi | |
| 6,066,125 A | 5/2000 | Webster, Jr. | |
| 6,120,476 A | 9/2000 | Fung et al. | |
| 6,235,022 B1 | 5/2001 | Hallock et al. | |
| 6,501,654 B2 | 12/2002 | O'Connor et al. | |
| 6,711,017 B2 | 3/2004 | Kurokawa et al. | |
| 6,893,432 B2 | 5/2005 | Intintoli et al. | |
| 7,127,033 B2 | 10/2006 | Lovoi et al. | |
| 7,377,906 B2 | 5/2008 | Selkee | |
| 7,400,502 B2 * | 7/2008 | Hamman | H01L 23/473 165/80.3 |
| 7,413,543 B2 | 8/2008 | Banik et al. | |
| 8,353,903 B2 * | 1/2013 | Podhajsky | A61B 18/1815 606/33 |
| 8,523,927 B2 * | 9/2013 | Levinson | A61F 7/10 606/20 |
| 2004/0116919 A1 | 6/2004 | Heim et al. | |
| 2006/0060333 A1 | 3/2006 | Chordia et al. | |
| 2006/0173344 A1 | 8/2006 | Marian et al. | |
| 2007/0156131 A1 | 7/2007 | Datta | |
| 2008/0147056 A1 | 6/2008 | van der Weide et al. | |
| 2009/0030411 A1 | 1/2009 | Werneth et al. | |
| 2009/0149850 A1 * | 6/2009 | Turovskiy | A61B 90/39 606/41 |
| 2010/0286681 A1 * | 11/2010 | Podhajsky | A61B 18/18 606/33 |
| 2010/0286683 A1 | 11/2010 | Podhajsky | |
| 2011/0152857 A1 | 6/2011 | Ingle | |

FOREIGN PATENT DOCUMENTS

| | | |
|---|---|---|
| JP | 2007-181695 A | 7/2007 |
| JP | 2007-535370 A | 12/2007 |
| JP | 2008-502137 A | 1/2008 |
| JP | 2008-136875 A | 6/2008 |
| WO | WO 01/06941 A1 | 2/2001 |
| WO | WO 2005/110265 A2 | 11/2005 |
| WO | WO 2005/121681 A2 | 12/2005 |
| WO | WO 2010/129348 A1 | 11/2010 |

OTHER PUBLICATIONS

European Search Report dated Feb. 10, 2012 from European Patent Application No. EP 11188260.1 (2 pages).
SIPO Office action (English translation) dated Nov. 15, 2014, issued in CN Application No. 201110373828.8 (4 pages).
Chinese Patent Office action dated Sep. 18, 2015 in corresponding CN application No. 201110373828.8 (3 pages).
English Language Translation of Japanese Patent Office Notification of Reasons for Refusal issued in Japanese Patent Application No. 2011-244181, dated Jul. 28, 2015 (5 pages).

* cited by examiner

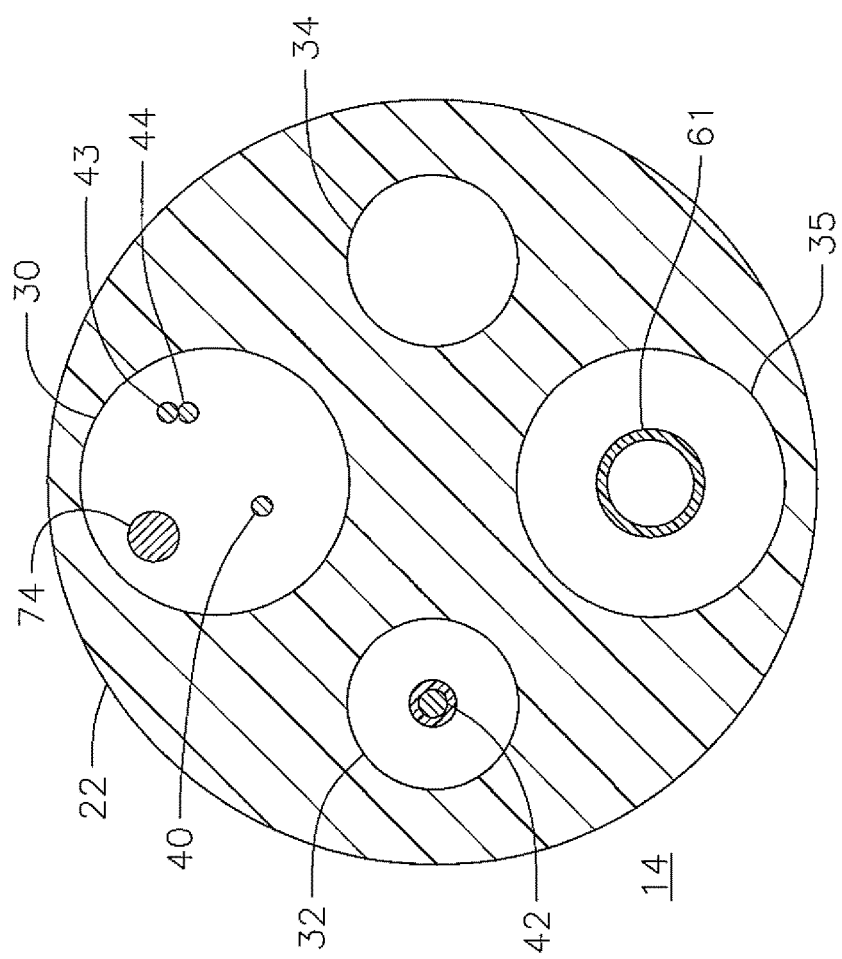

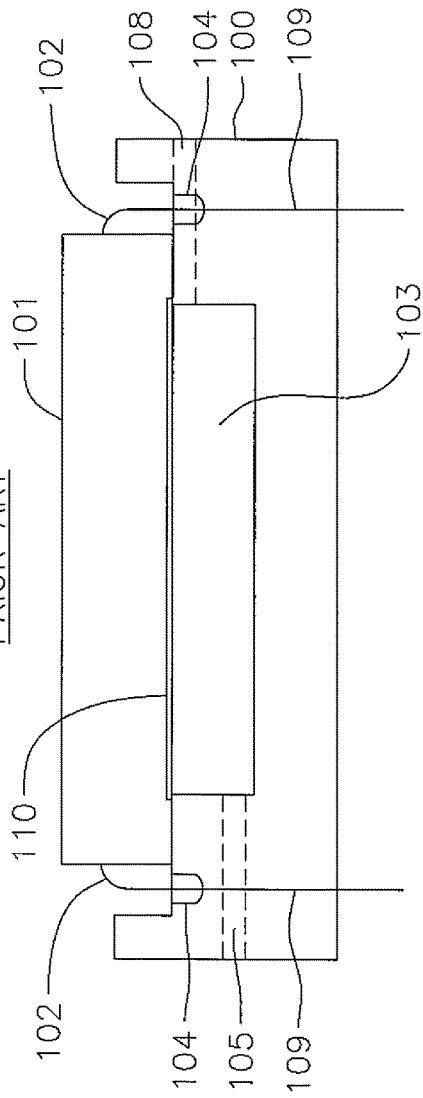
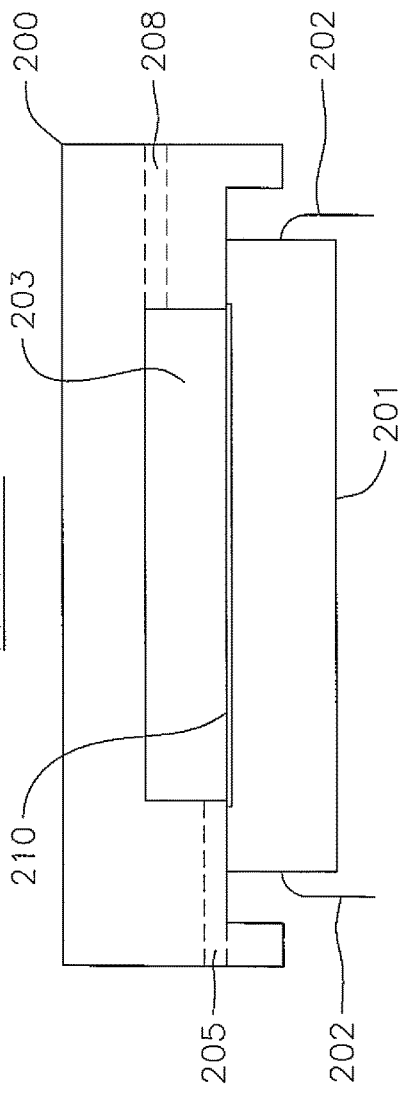
FIG. 7A PRIOR ART
FIG. 7B PRIOR ART

CATHETER WITH LIQUID-COOLED CONTROL HANDLE

CROSS-REFERENCE TO RELATED APPLICATION(S)

This application is a continuation of, and claims priority to and the benefit of, U.S. application Ser. No. 14/666,247 filed Mar. 23, 2015, now U.S. Pat. No. 9,289,259, which is a continuation of, and claims priority to and the benefit of, U.S. patent application Ser. No. 12/942,880 filed Nov. 9, 2010, now U.S. Pat. No. 8,986,303, the entire contents of which are incorporated herein by reference.

BACKGROUND

The present invention relates to catheters and, in particular, to a catheter with an improved control handle.

FIELD OF INVENTION

Catheters have been in common use in medical practice for many years. Applications of catheters include stimulating and mapping electrical activity in the heart and ablating sites of aberrant electrical activity. Such catheters are also referred to as electrode catheters. In use, an electrode catheter is inserted into a major vein or artery, e.g., femoral artery, and then guided into the location of interest within the body, e.g., the chamber of the heart where aberrant electrical activity within the heart is located.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. Lesions created by such cardiac ablation procedure effectively interrupt errant electrical pathways in the heart.

Catheters typically have an elongated catheter body, a deflectable section distal the catheter body and tip section distal the deflectable section. A typical ablation catheter provides irrigation at the tip electrode for a number of reasons, including the avoidance of charring and the desire for larger lesions. By irrigating the ablation electrode, such as with room temperature physiologic saline, the ablation electrode is actively cooled instead of more passive physiological cooling by blood flow. Because the strength of the RF current is no longer limited by the interface temperature, current can be increased for larger and more spherical lesions.

A control handle proximal the catheter body serves primarily to house deflection mechanism coupled to puller wires extending through catheter and provide an interface by which a user can manipulate the deflection mechanism. Where irrigation is provided, an irrigation tubing extends through the control handle to pass fluid from a fluid source to a distal end of the catheter. The control handle also normally houses a printed circuit board supporting various circuits and chips configured for signal processing from and/or to the distal section or tip electrode, including, for example, amplification of signals from an electromagnetic position sensor and/or digitizing circuits for digitizing a voltage signal of the thermocouple. An EPROM chip may also be included to shut down the circuit board after the catheter has been used so as to prevent reuse of the catheter, or at least the electromagnetic sensor.

Current catheters with a control handle containing a PC board rely on natural convection within a closed chamber of the control handle to provide cooling of the PC board. As catheters become more advanced and capable, the internal electronics become more involved, often resulting in greater thermal waste energy loads. Increases in thermal waster energy result in increased thermal temperatures in the control handle and ultimately high handle temperatures which can negatively affect user comfort.

Small fans are often used on PC boards to increase the convective heat loss of the board. However, because control handles are typically sealed, the heat load will increase the handle temperature. In order for fans to be effective in a catheter handle, inlet and outlet grates or ports should be integrated into the catheter handle. But such features may diminish the aesthetics of the handle. Heat pipes can also be integrated into the handle to increase heat transfer from the mounted integrated circuits, but again the heat will tend to remain in the handle increasing handle temperature. Self pumping micro fluidic heat exchangers may also be used but, like heat pipes, they will release heat energy into the handle resulting in increased handle temperatures.

As irrigation fluid at room temperature ranges between about 20-25 C (or 68-77 F), which is significantly lower than the normal human body temperature of 37 C (or 98.6 F), and it is known to pass irrigation fluid through the control handle, it would be desirable to provide an improved control handle that uses the irrigation fluid flowing therethrough to help cool the PC board and lower the temperature inside the control handle by transporting the heat out of the control handle. Such increased heat transfer will result in lower operating temperature of the PC board and hence a cooler control handle.

SUMMARY

The present invention is directed to an electrophysiologic catheter adapted for use in a patient's heart with an improved control handle. Catheters typically have a catheter body and a control handle which houses a heat source, including integrated circuits mounted on a printed circuit board, which can produce undesirable thermal waste energy loads that accumulate in the control handle causing discomfort to a user. In accordance with a feature of the present invention, the catheter includes a heat transfer assembly to better dissipate heat in the control handle. The heat transfer assembly includes a pump, a reservoir containing a coolant, a heat transfer member, and a coolant transport network transporting coolant between at least the reservoir and the heat transfer member. In one embodiment, the heat transfer member is located within the control handle as a heat exchanger on the circuit board to receive the coolant for transferring heat from the integrated circuits to the coolant. In another embodiment, at least one heat transfer member is located on the circuit board directly surrounding the integrated circuits to internally cool the integrated circuit within the control handle. A second heat transfer member is located outside of the control handle as a heat exchanger. The heat transfer member of this embodiment may be an IC heat transfer unit, a cover heat transfer unit or a heat transfer assembly. Either embodiment may be configured with a closed a coolant transport network or an open coolant transport network.

BRIEF DESCRIPTION OF THE DRAWINGS

The features and aspects of the present invention will be more apparent from the following detailed description in conjunction with the accompanying drawings, in which:

FIG. 2C is an end cross-sectional view of the catheter of FIGS. 2A and 2B, taken along line C-C.

FIG. 7a is a side view of a heat transfer member in the form of an IC heat transfer unit of the present invention, according to one embodiment.

FIG. 7b is a side view of a heat transfer member in the form of a cover heat transfer unit of the present invention, according to one embodiment.

DETAILED DESCRIPTION

Embodiments of the present invention will be described more fully hereinafter, in which exemplary embodiments are shown. This disclosure may, however, be embodied in many different forms and is not be construed as limited to the exemplary embodiments set forth herein. Here, when a first element is described as being coupled or connected to a second element, the first element may be directly connected to the second element or indirectly connected to the second element via one or more third elements.

Figure 1:
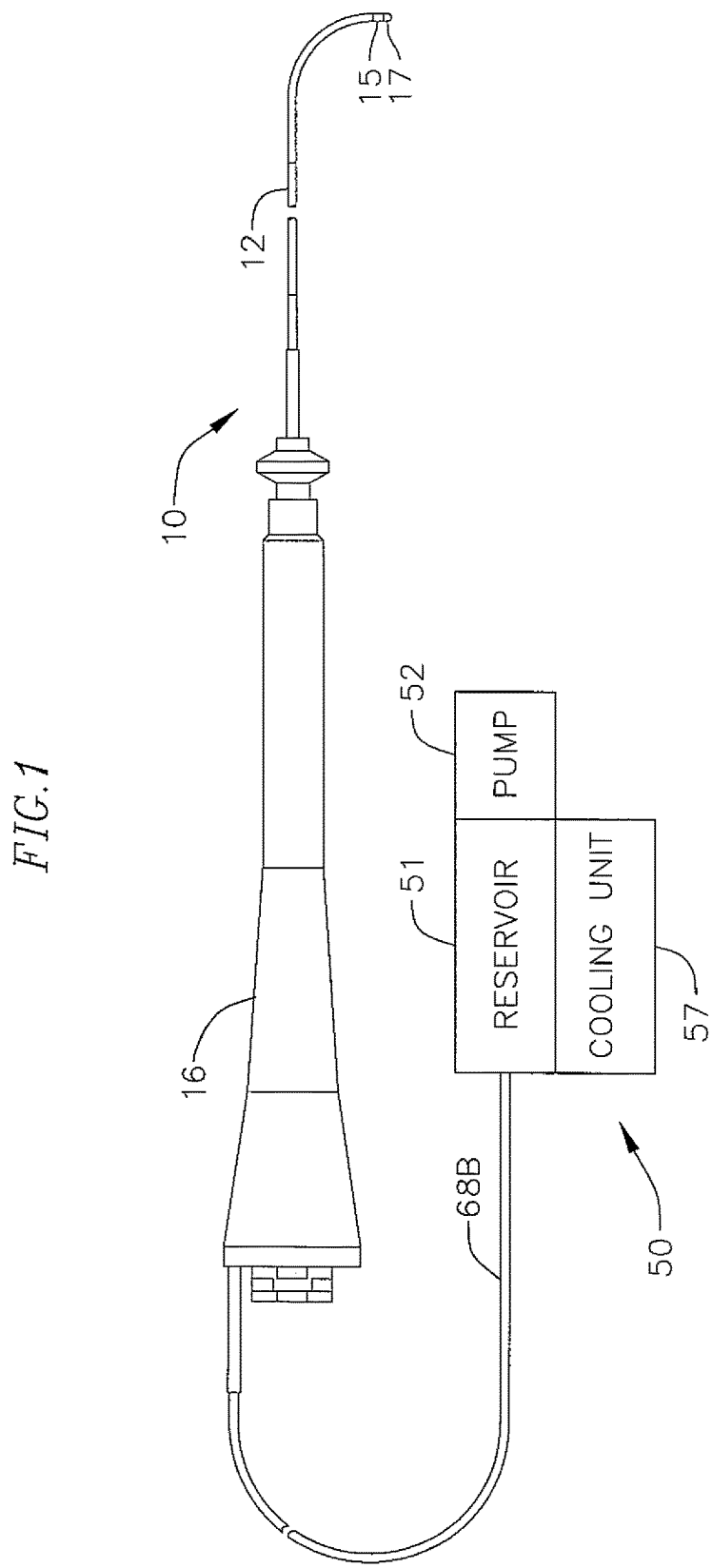
FIG. 1 is a schematic diagram of a catheter, including a heat transfer assembly, according to an embodiment of the present invention.

FIG. 1 illustrates a catheter 10 according to an embodiment of the present invention. The catheter 10 includes an elongated catheter shaft or body 12 having proximal and distal ends, an intermediate section 14 with uni- or bi-directional deflection distal of the catheter shaft 12, a tip section 15 with a tip electrode 17 at a distal end of the intermediate section, and a control handle 16 at the proximal end of the catheter shaft 12. Advantageously, the catheter includes a heat transfer assembly employing a reservoir of coolant and a pump to provide cooling of integrated circuits housed in the control handle by means of forced convection.

Figure 2A:
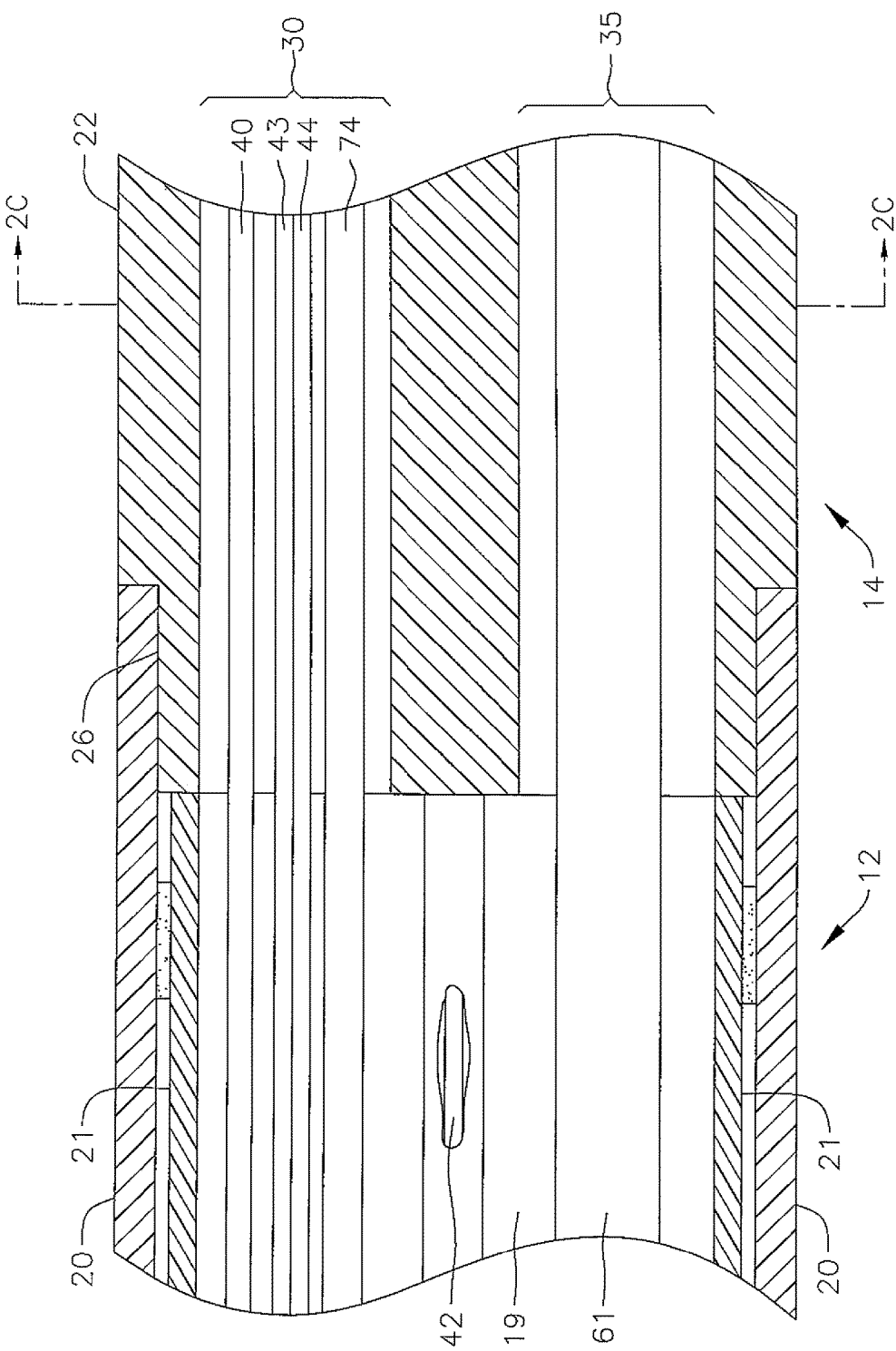
FIG. 2A is a side cross-sectional view of the catheter of FIG. 1, including a junction of a catheter body and an intermediate section, along a first diameter.
Figure 2B:
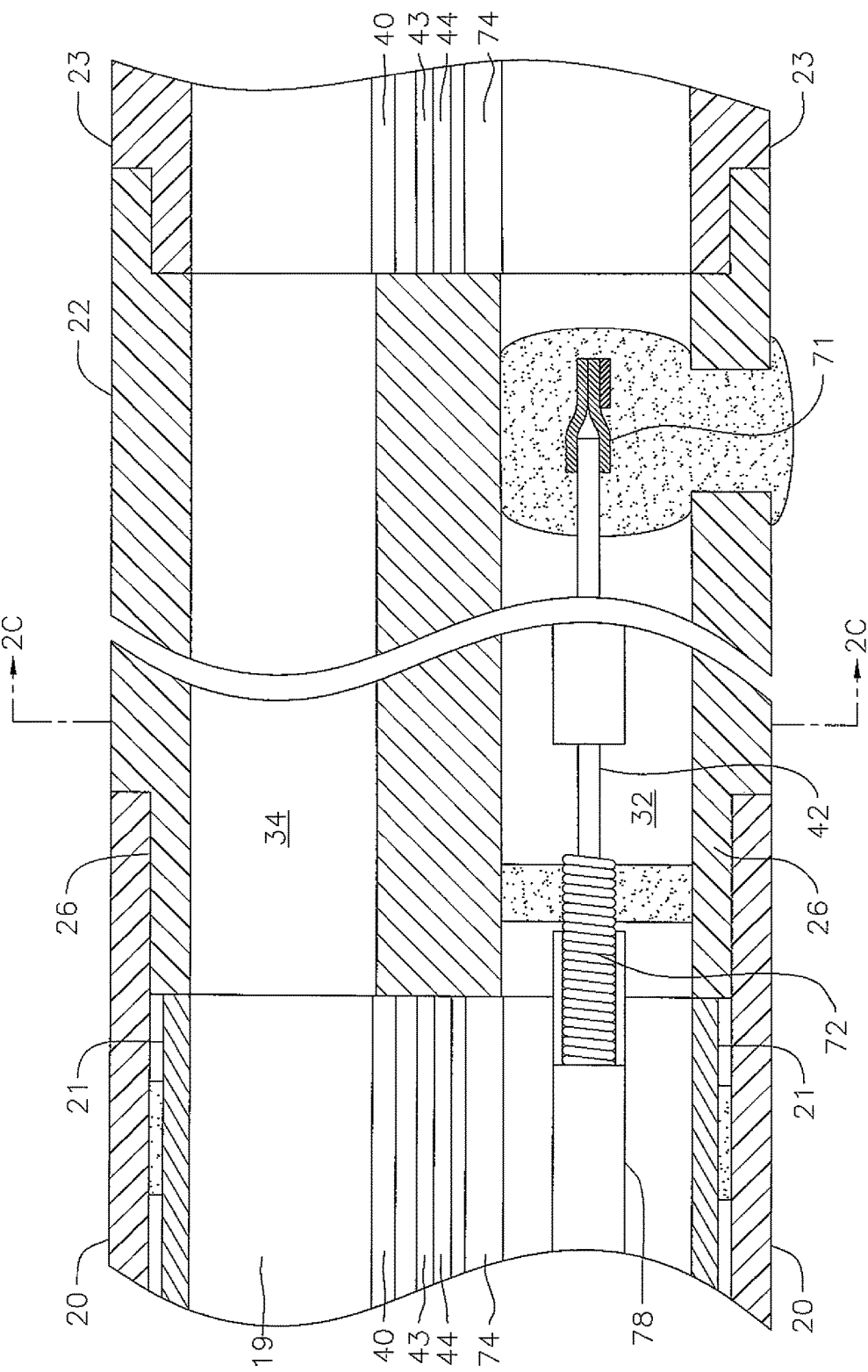
FIG. 2B is a side cross-sectional view of the catheter of FIG. 1, including a junction of a catheter body and an intermediate section, along a second diameter generally perpendicular to the first diameter.

As shown in FIGS. 2A and 2B, the catheter body 12 comprises an elongated tubular construction having a single, axial or central lumen 19. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an embedded braided mesh of stainless steel or the like to increase torsional stiffness of the catheter body 12 so that, when the control handle 16 is rotated, the intermediate section 14 of the catheter 10 is able to rotate in a corresponding manner.

The outer diameter of the catheter body 12 is not critical, but is preferably no more than about 9 french, more preferably about 7 french. Likewise, the thickness of the outer wall 20 is not critical, but is thin enough so that the central lumen 19 can accommodate puller wires, one or more lead wires, and any other desired wires, cables or tubes. If desired, the inner surface of the outer wall 20 is lined with a stiffening tube 21 to provide improved torsional stability. In one embodiment, catheter 10 has an outer wall 20 with an outer diameter of from about 0.090 inches to about 0.094 inches and an inner diameter of from about 0.061 inches to about 0.065 inches.

The intermediate section 14 comprises a short section of tubing 22 having multiple lumens, as also shown in FIG. 2C. In one embodiment, a first lumen 30 carries one or more lead wires 50, temperature sensor (e.g., thermocouple wires 43 and 44) for monitoring tissue temperature in the tip electrode 17, and a cable 74 for an electromagnetic position 75 sensor housed in the tip section 14. A second lumen 32 carries a puller wire for at least deflection along one direction in a plane. An opposing third lumen 34 can carry a second puller wire if bi-directional deflection along a second, opposing direction in the plane of the first deflection is desired. A fourth lumen 35 carries an irrigation tube 61 for supplying fluid to the tip electrode. The tubing 22 is made of a suitable non-toxic material that is preferably more flexible than the catheter body 12. In one embodiment, the tubing 22 is braided polyurethane, i.e., polyurethane with an embedded mesh of braided stainless steel or the like. The number of lumens or the size of each lumen is not critical, but is sufficient to house the lead wires, puller wire(s), electromagnetic sensor cable, thermocouple wires and/or irrigation tubing depending on the embodiment.

A preferred means for attaching the catheter body 12 to the intermediate section 14 is illustrated in FIGS. 2A and 2B. The proximal end of the intermediate section 14 comprises an outer circumferential notch 26 that receives the inner surface of the outer wall 20 of the catheter body 12. The intermediate section 14 and catheter body 12 are attached by glue or the like.

If desired, a spacer (not shown) can be located within the catheter body 12 between the distal end of the stiffening tube 21 and the proximal end of the intermediate section 14. The spacer provides a transition in flexibility at the junction of the catheter body and intermediate section, which allows the junction to bend smoothly without folding or kinking. A catheter having such a spacer is described in U.S. Pat. No. 5,964,757, the entire disclosure of which is incorporated herein by reference.

Figure 3:
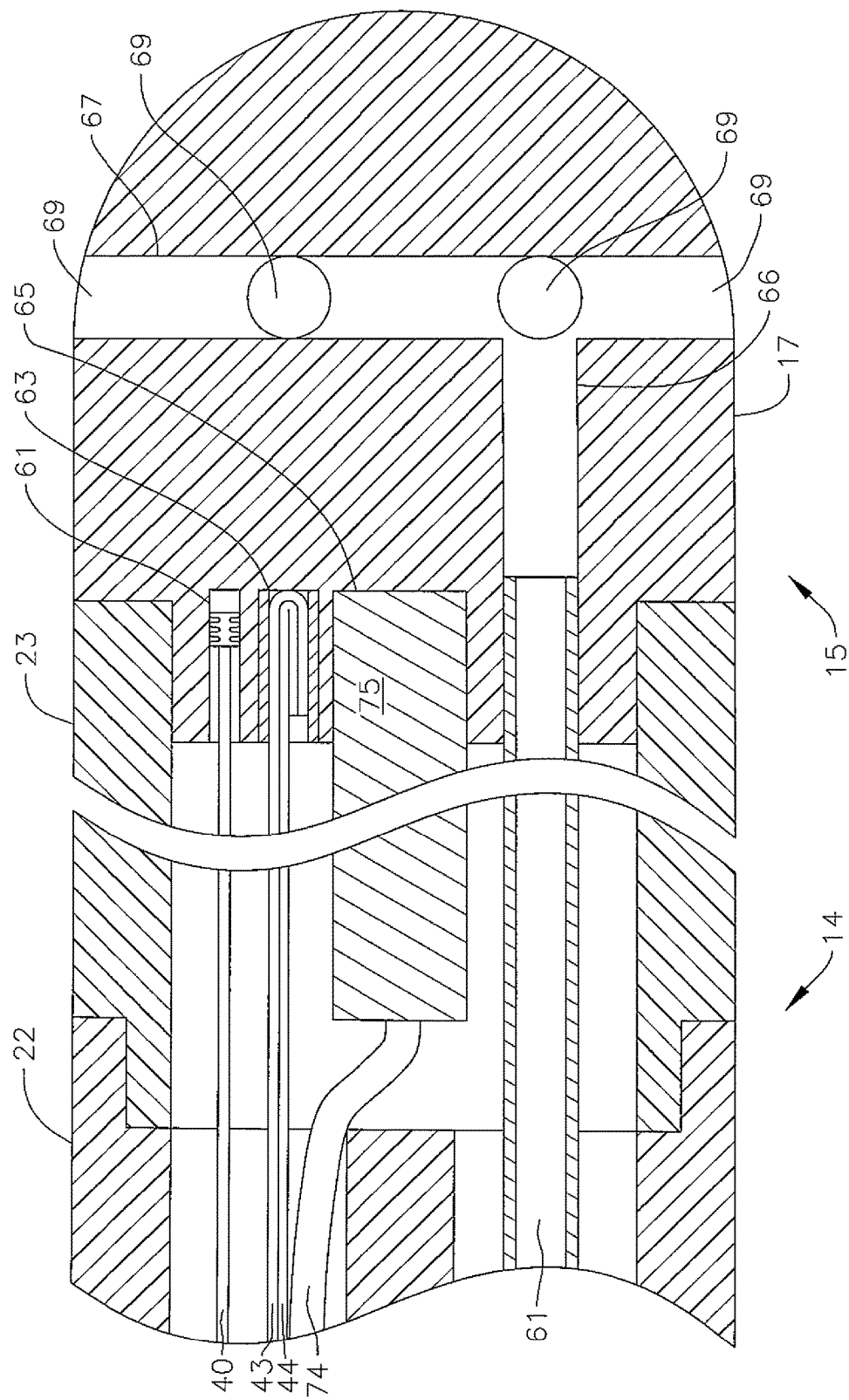
FIG. 3 is a side cross-sectional view of the catheter of FIG. 1, including a junction between an intermediate section and a connector tubing, with a tip electrode.

As illustrated in FIG. 3, the tip section 15 includes the tip electrode 17 which may be connected to the tubing 22 of the intermediate section 14 by means of a single lumen connector tubing 23. The connector tubing provides space for the electromagnetic position sensor 75 and the various components extending from the tubing 22 to reorient themselves as needed for anchoring in the tip electrode 17. To that end, a distal surface of the tip electrode is provided with blind holes. In the disclosed embodiment, blind hole 61 is provided to receive a distal end of the tip electrode lead wire 40, blind hole 63 to receive a distal end of the thermocouple wires 43 and 44, and blind hole 65 to receive a distal end of the electromagnetic sensor 75. Irrigation passage 66 is also formed in the tip electrode to receive a distal end of the irrigation tubing 61. The passage 66 is in communication with transverse branches 67 and fluid ports 69 allowing fluid delivered through the tubing 61 to pass to outside of the tip electrode.

As shown in FIG. 2B, the puller wire 42 is provided for uni-directional deflection of the intermediate section 14. The puller wire 42 extends through the catheter body 12, and is anchored at its proximal end to the control handle 16, and at its distal end to the tubing 22 near the distal end of the intermediate section 14 by means of a T-bar anchor 71, as generally described in U.S. Pat. Nos. 5,893,885 and 6,066,125, the entire disclosures of which are incorporated herein by reference. The puller wire is made of any suitable metal, such as stainless steel or Nitinol, and are preferably coated with Teflon® or the like. The coating imparts lubricity to the puller wire 42. The puller wire 42 preferably has a diameter ranging from about 0.006 to about 0.010 inch.

A compression coil 72 is situated within the catheter body 12 in surrounding relation to the puller wire 42, as shown in FIG. 2B. The compression coil 72 extends from the proximal end of the catheter body 12 to the proximal end of the intermediate section 14. The compression coil is made of any suitable metal, preferably stainless steel and is tightly wound on itself to provide flexibility, i.e., bending, but to resist compression. The inner diameter of the compression coil is preferably slightly larger than the diameter of the puller wire. The Teflon® coating on the puller wire allows it to slide freely within the compression coil. The outer surface of the compression coil is covered by a flexible, non-conductive sheath 78, e.g., made of polyimide tubing.

Figure 4:
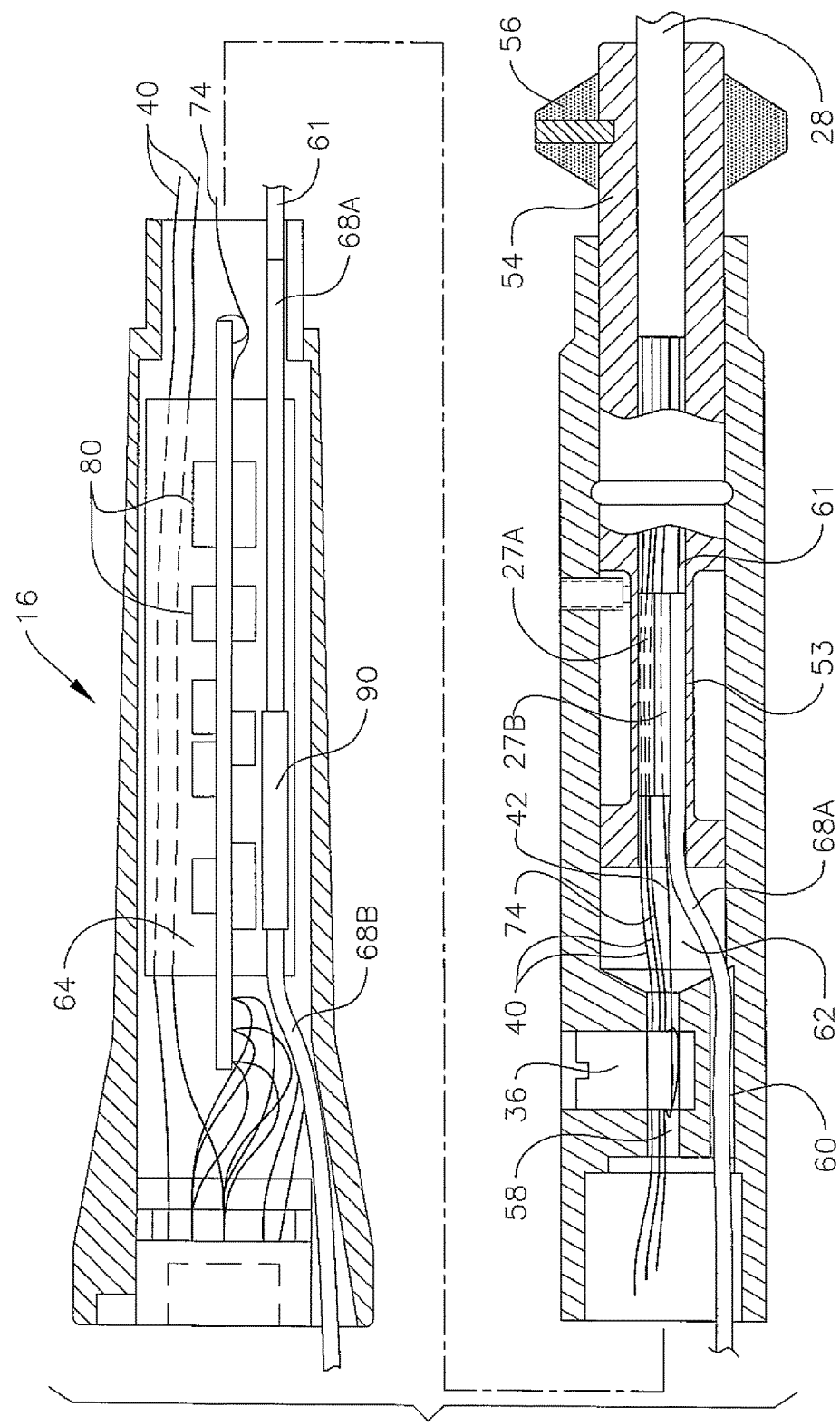
FIG. 4 is a side cross-sectional view of the control handle of FIG. 1, including a piston with a thumb control.

Longitudinal movement of the puller wire 42 relative to the catheter body 12, which results in deflection of the intermediate section 14, is accomplished by suitable manipulation of the control handle 16. Examples of suitable control handles for use in the present invention are disclosed in U.S. Pat. Nos. Re 34,502, 5,897,529, and 7,377,906, the entire disclosures of which are incorporated herein by reference. In the embodiment of FIG. 4, a distal end of the control handle 16 comprises a piston 54 with a thumb control 56 for manipulating the puller wire 42 for uni-directional deflection of the intermediate section 14, although it is understood that the present invention is readily adaptable to a control handle with two puller wires for bi-directional deflection.

Connected to the piston 54 by means of a shrink sleeve 28 is the proximal end of the catheter body 12. The irrigation tubing 61, the puller wire 42, the lead wire 40, the thermocouple wires 43 and 44 and the electromagnetic sensor cable 74 extend proximally from the catheter body through the piston 54. The puller wire 42 is anchored to an anchor pin 36 located proximal to the piston 54. The lead wire 40, thermocouple wires 43 and 44 and electromagnetic sensor cable 74 extend through a first tunnel 58, located near the side of the control handle 16. The electromagnetic sensor cable 74 connects to a circuit board 64 in the proximal end of the control handle. Wires 73 connect the circuit board 64 to, for example, a mapping and/or ablation system, including a computer and imaging monitor (not shown).

Within the piston 54, the electromagnetic sensor cable 74 and lead wires 40 are situated within a transfer tube 27a, and the puller wire 42 is situated within another transfer tube 27b to allow longitudinal movement of the wire and cable near the glue joint 53. The irrigation tubing 61 extends proximally through the shrink sleeve 28 where its proximal end is in communication with the heat transfer assembly 50 via a distal conduit 68a which extends through a second tunnel 60 situated near the side of the piston 54 opposite the anchor pin 36.

The control handle 16 houses a heat source, including the printed circuit (PC) board 64 on which are mounted multiple integrated circuits serving various functions such as local amplification and/or processing of signals, including signals from the electromagnetic sensor and/or the thermocouple housed in the distal section of the catheter. An EPROM chip may also be included to limit the catheter or at least the position sensor to a single use.

In the embodiment of FIGS. 1 and 4, the heat transfer assembly 50 is configured as an open system employing the reservoir 51 and the pump 52 (e.g., an infusion pump), a coolant transport network with fluid conduits 68a and 68b, and/or other mechanisms and components typically employed for delivering fluid through the catheter to the tip electrode. As described above, irrigation fluid is delivered in the irrigation tubing 61 of the catheter 10. In the present invention, the heat transfer assembly advantageously uses the fluid, e.g., irrigation saline, as a coolant to cool the PC board in the control handle. In the embodiment illustrated in FIG. 1, the infusion pump 52 pumps the fluid from the reservoir 51 through the proximal fluid conduit 68*b* passing into the control handle 16. A distal end of the conduit 68b terminates at and feeds into an inlet of a heat transfer unit, for example, a heat exchanger 90 (or heat sink) mounted on or near integrated circuits 80 on the PC board 64, especially high power output integrated circuits. An outlet of the heat exchanger feeds to a proximal end of the distal fluid conduit 68 *a* whose distal end is in communication with a proximal end of the irrigation tubing 61 inside the piston 54. As shown in FIG. 4, the distal fluid conduit 68 *a* is anchored to the inside of the control handle 16 by glue joint 53.

The heat transfer assembly 50 applies the principle of forced convection to cool the PC board 64 and hence the control handle 16. As the integrated circuits 80 on the PC board heat up during use of the catheter, the heat generated is transferred to the heat exchanger 90. As irrigation fluid transported by the proximal conduit 68b flows through the heat exchanger 90, the heat transferred to the heat exchanger is further transferred to the fluid thereby cooling the heat exchanger.

As understood in the art, the heat exchanger 90 is configured to dissipate thermal waste energy from the PC board 64 to the irrigation fluid from the reservoir 51 by maximizing surface area between the open space in the control handle and the irrigation fluid, while minimizing resistance to fluid flow through the heat exchanger 90. The heat exchanger can take any suitable form, including a plate heat exchanger or a tubular heat exchanger, with parallel-flow, counter-flow, or cross-flow as desired or appropriate. The heat exchanger is constructed of any suitable material that is thermally conductive for optimal heat transfer. The material should also be biocompatible and suitable for ETO sterilization, including, for example, stainless steel or noble metal plated copper, such that contact between the irrigation fluid and the heat exchanger material does not compromise the fluid in terms of sterility and biocompatibility when it exits from the ports in the tip electrode and enters the patient's body.

Where the irrigation fluid is at room temperature, for example, ranging between about 20-25 C (or 68-77 F), the heat exchanger 90 can be expected to raise the temperature of the fluid by about 5 degrees, to about 25-30 C or (77-86 F). Since normal human body temperature is about 37 C (or 98.6 F), there is little risk of introducing overheated fluid into the patient, or of overheating the patient over the course of the catheter procedure. However, if desired, temperature control over the fluid can be provided by means of a cooling unit 57, including, for example, a radiator, a compressor, and an expansion valve, that pre-cools the fluid from the reservoir by a predetermined amount before it enters the control handle and the heat exchanger so that the temperature of the fluid exiting the heat exchanger and/or the control handle is generally predetermined before it exits the tip electrode and enters the patient's body.

Figure 5:
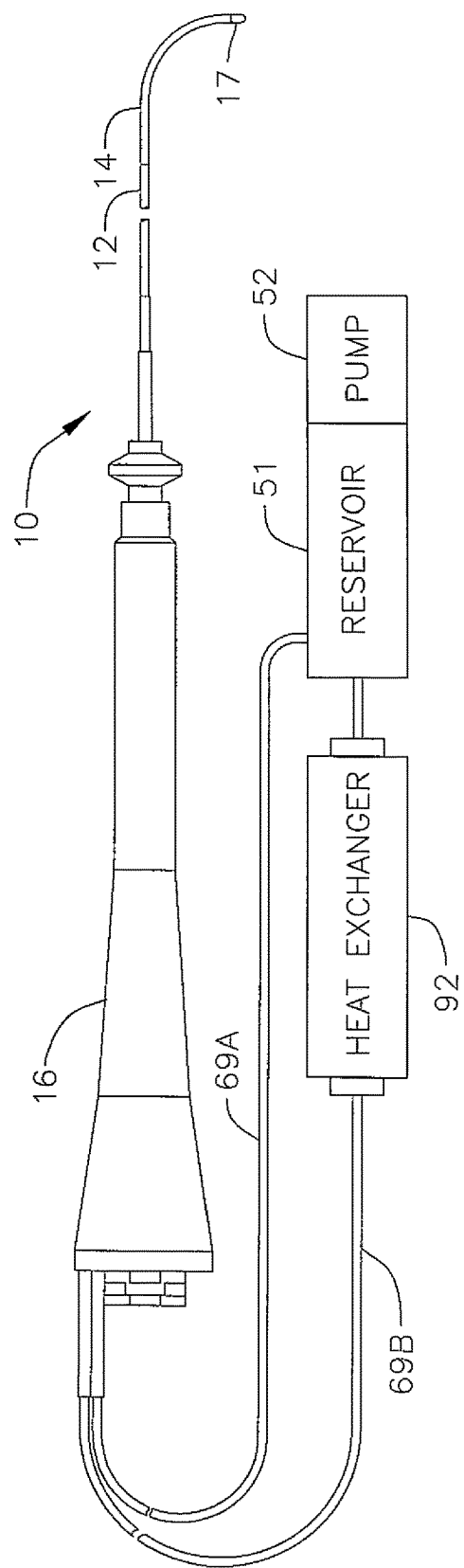
FIG. 5 is a schematic diagram of a catheter, including a heat transfer assembly, according to an alternate embodiment of the present invention.
Figure 6:
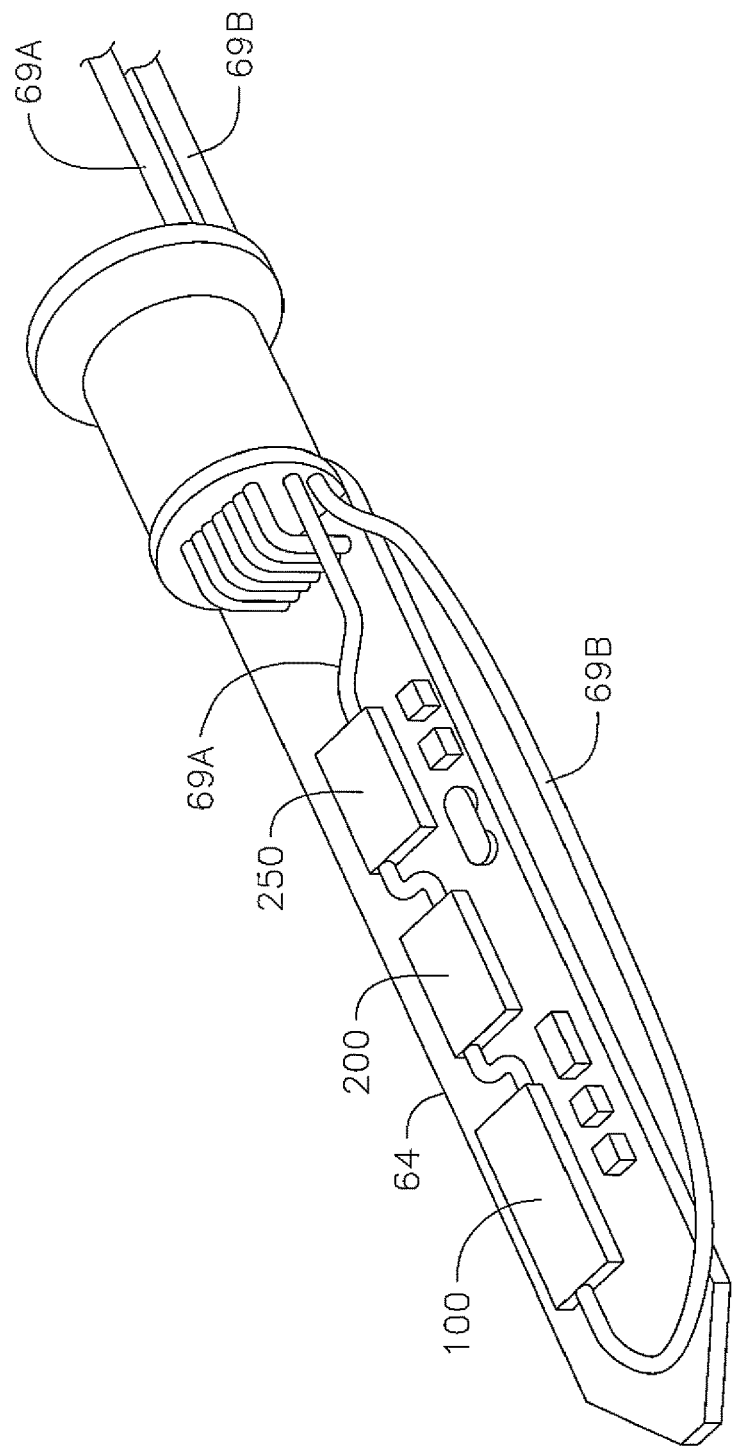
FIG. 6 is an perspective view of a printed circuit board within a control handle of the catheter of FIG. 5, according to one embodiment of the present invention.

In an alternate embodiment shown in FIG. 5, a heat transfer assembly 50*a* is configured as a closed system, wherein the coolant is recirculated by the coolant transport network between one or more heat transfer units, such as IC heat transfer units 100, 200 and/or 250 provided on the PC board 64, and a remote heat exchanger 92 connected via a coolant feed conduit 69*b* and a coolant return conduit 69*a*. Coolant-cooled integrated circuits are known in the art and are described in U.S. Pat. Nos. 7,400,502 and 5,360,993, the entire contents of which are incorporated by reference. FIG. 7*a* illustrates an embodiment of a connector heat transfer unit (or hereinafter an IC heat transfer unit) 100 of the prior art, which is depicted with a heat generating component 101, such as an integrated circuit or chip, inserted into the connector heat transfer unit 100. The IC heat transfer unit 100 may be of a variety of shapes and sizes, but these will be determined principally by the size and electrical conductor configuration of the heat generating component and the motherboard (or PC board) to which the connector heat transfer unit will be coupled. All of the following embodiments of the IC heat transfer unit can be deployed in an application where the IC heat transfer unit is not mechanically attached to any type of motherboard and, it will be understood, that the IC heat transfer unit may be electrically connected to the mother board in any suitable manner. The IC heat transfer unit may be composed of any number of materials but a lightweight, electrical insulating material is desirable.

In FIG. 7*a*, the electrical conductors or pins 102 of the chip 101 are inserted into receptacles 104. A cavity 103 is disposed in the IC heat transfer unit 100 such that a surface of the cavity in thermally coupled to the surface of the chip 101. This surface of the cavity may be composed of any good heat conducting material, such as copper, to transfer heat from the heat generating component to a coolant flowing through the cavity. The heat transfer unit 101 is configured with an inlet pathway 106 and an outlet pathway 108 for fluid entry and exit from the cavity. As understood by one of ordinary skill in the art, the configuration of the cavity and the pathways can be varied as needed or desired to alter fluid flow efficiency.

The IC heat transfer unit pins 109 electrically connect the receptacles 104 to the PC board, for example, by soldering. It will be appreciated that any suitable means may be used to connect the pins of chip 101 to the PC board and the IC heat transfer unit is not limited to the receptacles 104 and pins 109 described above. For example, the connector heat transfer unit 100 may have a plurality of holes for pins 102 to be inserted into and through and then soldered to the PC board.

The surface of the cavity 103, thermally coupled to the heat generating component 101, is depicted as 110. The surface 110 may be comprised of any good heat conducting material, such as copper. This surface 110 is preferably coupled to the heat generating component 101 by means of a thermal paste having good thermal transfer characteristics. Alternatively, the heat generating component 101 may be held in place within the connector heat transfer unit 100 and thermal coupling of the component 101 to the surface 110 achieved by use of one or more clips, not shown, from the connector heat transfer unit 100 to the component 101 or by a one or more clamp assemblies, not shown. In any case, it is preferable to apply thermal paste to the coupling of surface 110 with the component to insure maximum heat transfer. It should also be appreciated that the present invention encompasses many other possibilities for thermally coupling the component 101 to the surface 110 including, but not limited to, application of mechanical force, such as a clamping motion, to create a positive force between the component 101 and the surface 110 and thus improve thermal conductivity.

The electrical conductors or pins 102 of most commercial heat generating components, such as microprocessors, for example, are typically copper coated with precious metals. Thus, in addition to being good electrical conductors, they are also good heat conductors. Similarly, the receptacles 104 and electrical conductors or pins 109 may be comprised of similar materials with both good electrical and heat transfer characteristics. The IC heat transfer unit 100 may then be comprised of a material with good electrical insulation characteristics and good heat transfer characteristics to provide cooling and/or additional cooling of the chip 101. A wide variety of materials, such as a hard silicone, for example, can be used for this purpose in the IC heat transfer unit 100. Specifically, heat from the chip 101 is transferred to the electrical conductors or pins 102. Some of this heat may be transferred from the pins 102, directly and/or indirectly through the receptacles 104 and pins 109, for example, to the IC heat transfer unit 100 and then on to the cavity 103 where the coolant flowing there through will absorb some or all of this heat for dissipation. A thermal paste can be applied to the electrical conductors or pins 102 to insure maximum heat transfer to the body of the IC heat transfer unit 100 directly, or indirectly through the receptacles 104 and pins 109, for example. It should also be appreciated that pins 102 and the IC heat transfer unit 100 can be thermally coupled via other means including, but not limited to, application of mechanical force to create pressure in a clamping motion.

In yet another alternative for coupling the surface 110 to the chip 101, the surface 110 may be open or partially open allowing the coolant to come into direct contact with the chip 101, which normally is encased and protected by an IC pack (not shown) and thereby eliminating the thermal resistance of both the surface 110 and the thermal paste or other thermal connection medium used. In this situation, for example, the surface 110 could be in the form of a flange around the perimeter of the cavity 103. When the flange is coupled and sealed to the chip 101, the cavity is sealed and coolant will come in direct contact with the chip 101 without leaks or spills.

Referring now to FIG. 7*b*, a cover heat transfer unit 200 for the IC heat transfer unit 100 is depicted which provides additional cooling of the chip 101. The cover heat transfer unit 200 has many similarities to the IC heat transfer unit 100, including a cavity 203. Entrances and exits for the coolant to and from the cavity 203 are provided by inlet pathway 206 and by outlet pathway 208, respectively. The electrical conductors or pins 202 of the chip 101 are shown. Cavity 203 has a surface 210 which is thermally coupled to the chip 101.

Whenever possible, it is desirable to orient the heat transfer units 100 and 200 so that the respective inlet is situated below the respective outlet. This orientation allows the cooling system to take advantage of convective circulation of the coolant since heated coolant will naturally rise and cooled coolant will naturally drop. In this manner, the thermodynamics of the coolant can assist forced circulation, by a pump for example, and provide additional cooling of the heat generating components even after power is shut down.

Figure 7C:
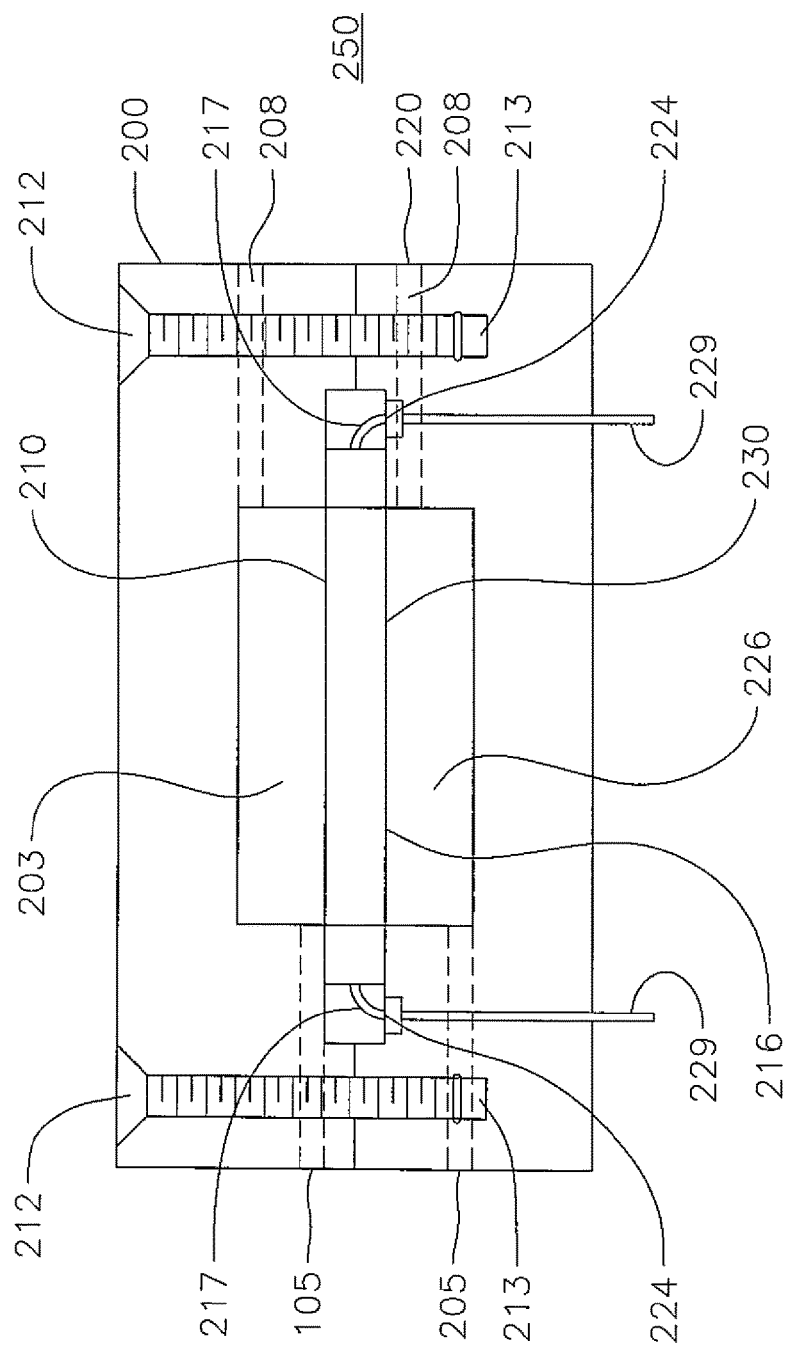
FIG. 7c is a side view of a heat transfer member in the form of a heat transfer assembly of the present invention, according to one embodiment.

A function of cover heat transfer unit 200 is to provide cooling to an additional surface of the chip 101. As shown in the embodiment of FIG. 7c, when a cover heat transfer unit 200 is used in conjunction with IC heat transfer unit 100 in forming a heat transfer module 250 to secure and cool a single chip, surface 210 is transferring heat from one side of the chip to a coolant while surface 110 is transferring heat from an opposite side of the chip to a coolant. Use of the cover heat transfer unit 200 then can provide dramatic increases in cooling power or capacity when combined with the IC heat transfer unit 100.

The IC heat transfer unit 220 includes a cavity 223; a surface 230 of the cavity 223 thermally coupled to the chip 216; a plurality of receptacles or electrical contacts 224 to accept electrically the electrical conductors 217 of the chip 216; and a plurality of pins or electrical conductors 229, electrically connecting the receptacles 224 to the PC board via, for example, by wave soldering.

The chip 216 may be held in place within the module 250 and thermal coupling of the component to the surfaces 110 and 210 achieved by any number of methods. For example, one or more screws 212 threaded into one or more mating receptacles 213 may be utilized. Alternatively, or in addition, one or more spring clips, or any of a variety of mechanical fasteners to create a clamping force, not shown, from the IC heat transfer unit 220 to the cover 200 and/or adhesives may be utilized. In any case, it is preferable to apply a thermally conductive material to the coupling of surface 230 with the component 216 and to the coupling of surface 210 to the opposite side of the chip 216 to insure maximum heat transfer.

In yet another alternative for coupling the surfaces 230 and 210 to the chip 216, either one or both of the surfaces 230 and 210 may be open or partially open allowing the coolant to come into direct contact with the chip 216 and thereby eliminating the thermal resistance of both the surfaces 230 and 210 and the thermal resistance of thermal paste or other thermal connection medium used. In this situation, for example, either or both of surfaces 230 and 210 could be in the form of a flange around the perimeter of the cavities 223 and 203, respectively. When the flanges are coupled and sealed to opposite sides of heat generating component 216, the cavities are sealed and coolant will come in direct contact with the component on opposite sides there of without leaks or spills.

In operation, cooled coolant received from a heat exchange unit is applied to inlet pathways 105 and 205. It flows through into the cavities 103 and 203. Heat from the chip 101 is absorbed into the coolant and heats the coolant. The heated coolant then flows through outlet pathways 108 and 208 and is then directed back to the heat exchange unit for cooling. It will be appreciated and understood that other methods of receiving the coolant, directing the coolant through and out of the heat transfer module 250 may be utilized.

The heat transfer assembly in a closed or isolated configuration allows for more selection of a coolant since the coolant is not entering the patient's body. A fluid with an ideal coefficient of variation (COV) for use includes Propylene-Glycol. When used with an irrigated catheter, such a closed or isolated configuration allows for higher mass flow rates of coolant resulting increased convective heat transfer and a decrease in the thermal load to irrigation fluid preventing possible loss in irrigation effectiveness at the tip electrode.

As understood by one of ordinary skill in the art, additional cooling mechanisms, such as air-cooled heat sinks or heat pipes for example (not shown), can be coupled to a free surface of the chip 101 to provide for additional cooling, if desired. It is further understood that the handle 16 and PC board may have any suitable shapes and sizes. As one of ordinary skill in the art, the location of the circuit board within the handle can vary depending on the structures and components within the handle, such as mechanisms for controlling deflection of the intermediate section 14 and various wires, cables and tubings that extend through the control handle and distally along the catheter shaft and beyond.

Figure 8:
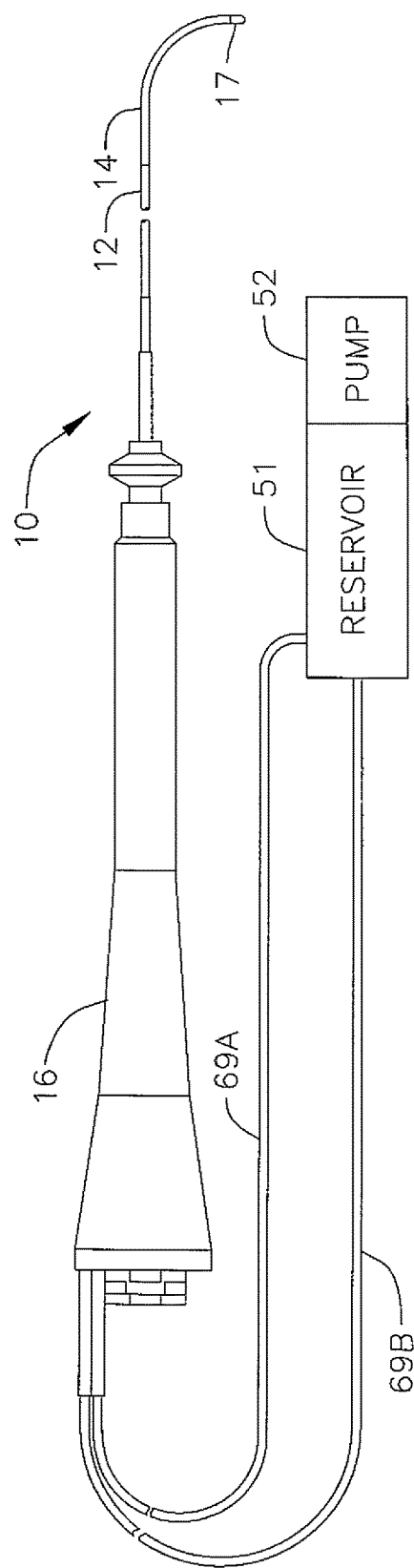
FIG. 8 is a schematic of a catheter, including a heat transfer assembly, according to another alternate embodiment of the present invention.
Figure 9:
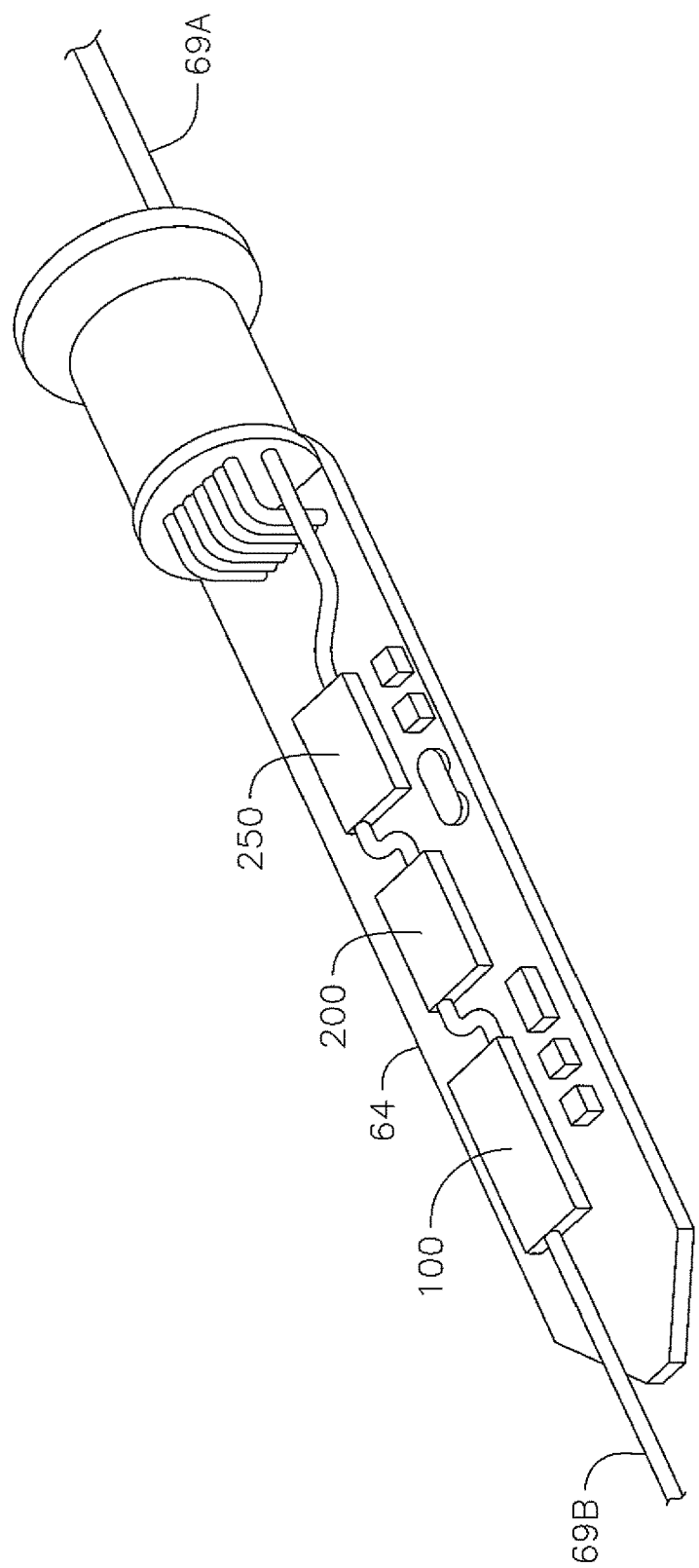
FIG. 9 is a schematic of a catheter, including a heat transfer assembly, according to yet another alternate embodiment of the present invention.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature of any one embodiment can be used in any other embodiment in the place of or in addition to other features. For example, although the first embodiment described herein features a catheter having an open system with a heat transfer assembly employing at least one heat exchanger mounted on the PC board and the second embodiment features a catheter having a closed system with at least one board-mounted heat transfer module, the present invention includes embodiments where the catheter has a closed system with a heat transfer assembly employing at least one heat exchanger mounted on the PC board (see FIG. 8), as well as a catheter having a open system with at least one board-mounted heat transfer module (see FIG. 9). As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:
1. An electrophysiologic catheter, comprising:
 a catheter body;
 a control handle proximal the catheter body, the control handle housing a printed circuit board on which is mounted one or more integrated circuits; and
 a heat transfer assembly including:
  a pump,
  a reservoir containing a coolant,
  a cooling unit configured to cool the coolant,
  a heat transfer member within the control handle and mounted on the printed circuit board, and a coolant transport network providing coolant communication between at least the reservoir or cooling unit and the heat transfer member mounted on the printed circuit board.

2. The catheter of claim 1, wherein the coolant transport network is configured as a closed network.

3. The catheter of claim 2, wherein the closed network comprises fluid communication from the reservoir or cooling unit to the heat transfer member within the control handle, and fluid communication from the heat transfer member within the control handle back to the reservoir or cooling unit.

4. The catheter of claim 1, wherein the coolant transport network is configured as an open network.

5. The catheter of claim 4, wherein the open network comprises fluid communication from the reservoir or cooling unit to the heat transfer member within the control handle, and fluid communication from the heat transfer member within the control handle to an irrigation tubing extending into the catheter body.

6. The catheter of claim 5, wherein the open network further comprises fluid communication from the irrigation tubing to outside the catheter body.

7. The catheter of claim 1, wherein the heat transfer member surrounds at least one of the one or more integrated circuits.

8. The catheter of claim 1, wherein the heat transfer member is a heat exchanger.

9. The catheter of claim 1, wherein the heat transfer member is an IC heat transfer unit.

10. The catheter of claim 1, wherein the heat transfer member is a cover heat transfer unit.

11. The catheter of claim 1, wherein the heat transfer member is a heat transfer module.

12. The catheter of claim 1, wherein the coolant transport network includes a conduit returning configured to return coolant from the heat transfer member to the cooling unit.

13. The catheter of claim 1, wherein the catheter includes a tip electrode, and an irrigation tubing configured to deliver coolant from the heat transfer unit to the tip electrode.

14. The catheter of claim 1, further comprising a heat exchanger external of the control handle, the coolant transport network providing fluid communication between the heat exchanger and the reservoir or cooling unit, and between the heat exchanger and the heat transfer member within the control handle.

15. The catheter of claim 1, wherein the heat transfer member comprises a plurality of heat transfer members in fluid communication with each other.

16. An electrophysiologic catheter, comprising:
a catheter body;
a control handle proximal the catheter body, the control handle housing a printed circuit board on which is mounted one or more integrated circuits; and
a heat transfer assembly including:
a pump,
a reservoir containing a coolant,
a cooling unit configured to cool the coolant,
one or more heat transfer members within the control handle and mounted on the printed circuit board,
an external heat exchanger outside the control handle, and
a coolant transport network providing coolant communication between the reservoir or cooling unit and the heat transfer member mounted on the printed circuit board, providing fluid communication between the external heat exchanger and the one or more heat transfer members within the control handle, and providing fluid communication between the reservoir or cooling unit and the external heat exchanger.

17. The catheter of claim 16, wherein the coolant transport network is a closed network comprising fluid communication from the reservoir or cooling unit to the heat transfer member within the control handle, fluid communication from the heat transfer member within the control handle to the external heat exchanger, and fluid communication from the external heat exchanger back to the reservoir or cooling unit.

18. An electrophysiologic catheter, comprising:
a catheter body;
a control handle proximal the catheter body, the control handle housing a printed circuit board on which is mounted one or more integrated circuits; and
a heat transfer assembly including:
a pump,
a reservoir containing a coolant,
one or more heat transfer members within the control handle and mounted on the printed circuit board,
an external heat exchanger outside the control handle, and
a coolant transport network providing coolant communication between the reservoir and the heat transfer member mounted on the printed circuit board, providing fluid communication between the external heat exchanger and the one or more heat transfer members within the control handle, and providing fluid communication between the reservoir and the external heat exchanger.

19. The catheter of claim 18, wherein the coolant transport network is a closed network comprising fluid communication from the reservoir to the heat transfer member within the control handle, fluid communication from the heat transfer member within the control handle to the external heat exchanger, and fluid communication from the external heat exchanger back to the reservoir.

* * * * *

UNITED STATES PATENT AND TRADEMARK OFFICE
CERTIFICATE OF CORRECTION

PATENT NO. : 10,213,254 B2  
APPLICATION NO. : 15/073510  
DATED : February 26, 2019  
INVENTOR(S) : Eduardo Jimenez et al.

Page 1 of 1

It is certified that error appears in the above-identified patent and that said Letters Patent is hereby corrected as shown below:

In the Claims

Column 11, Line 36, Claim 12     delete "returning configured" and insert -- configured --

Signed and Sealed this  
Third Day of November, 2020

Andrei Iancu  
*Director of the United States Patent and Trademark Office*